United States Patent [19]
Röss

[11] Patent Number: 4,458,979
[45] Date of Patent: Jul. 10, 1984

[54] LIGHT COLLECTING ARRANGEMENT IN COMBINATION WITH A LIGHT SCANNING ARRANGEMENT FOR INSPECTING A WEB OF MATERIAL

[75] Inventor: Dieter Röss, Planegg, Fed. Rep. of Germany

[73] Assignee: Erwin Sick GmbH Optik-Elektronik, Fed. Rep. of Germany

[21] Appl. No.: 235,360

[22] Filed: Feb. 17, 1981

[30] Foreign Application Priority Data

Feb. 19, 1980 [DE] Fed. Rep. of Germany ....... 3006071

[51] Int. Cl.³ .................. G03H 1/00; G01N 21/01
[52] U.S. Cl. ..................... 350/3.71; 356/431
[58] Field of Search .............. 350/162 R, 3.6, 3.7, 350/3.72, 3.71, 162.2

[56] References Cited

U.S. PATENT DOCUMENTS

| 3,728,117 | 4/1973 | Heidenhain et al. ........... 350/3.7 |
| 3,743,376 | 7/1973 | Russell ..................... 350/3.7 |

FOREIGN PATENT DOCUMENTS

| 2361626 | 11/1973 | Fed. Rep. of Germany . |
| 2329209 | 1/1974 | Fed. Rep. of Germany . |
| 2602970 | 7/1977 | Fed. Rep. of Germany . |
| 2150634 | 11/1977 | Fed. Rep. of Germany . |
| 2833261 | 10/1979 | Fed. Rep. of Germany . |

OTHER PUBLICATIONS

Sincerbox, G. T., *IBM Technical Disclosure Bulletin*, "Formation of Optical Elements by Holography", vol. 10, No. 3, Aug. 1967.

*Primary Examiner*—Bruce Y. Arnold
*Attorney, Agent, or Firm*—Townsend and Townsend

[57] ABSTRACT

A light collecting arrangement particularly for use with beam scanning apparatus for monitoring for faults in web material has a diffraction grating 11 and a light collecting surface usually in the form of photoelectric converter 19 arranged at right angles to the diffraction grating 11. The characteristics of the diffraction grating 11 are so selected that only light incident within a predetermined range is deflected to the light collecting surface. A number of different arrangements are disclosed. The light collecting arrangement can, for example, be used with a scanning light beam which is continuously displaced parallel to itself to effect point by point line by line scanning of the web material 17 or can take the form of a scanning light beam which executes a sector-like scanning movement. In the former case the diffraction grating should have a fixed grating constant in the latter case the grating constant should change along the length of the diffraction grating to compensate for the different angles of incidence which arise as a result of the sector-like movement of a scanning light beam. The diffraction grating 11 is conveniently in the form of a hologram and can conveniently be incorporated in a light conducting rod 14.

13 Claims, 11 Drawing Figures

LIGHT COLLECTING ARRANGEMENT IN COMBINATION WITH A LIGHT SCANNING ARRANGEMENT FOR INSPECTING A WEB OF MATERIAL

The invention relates to a light collecting arrangement having a light collecting surface and an elongate optical light deflecting device arranged substantially at right angles thereto for deflecting, in the direction of the light gathering surface, light beams which extend within a plane of incidence and which are incident at different points in the longitudinal direction with a significant component normal to the longitudinal direction at angles which lie within a predetermined range.

A light collecting arrangement in the sense of the present invention is intended to convert a light flux of large linear dimension and with restricted angular range which is present along a line into a shallow light flux with a large angular range so that a reduction of the exit surface is achieved in comparison to the entry surface. Known light collecting arrangements operate with mirror boxes, light conducting rods and/or diffuse reflecting hollow cavities (see for example German patent publications DE-OS No. 19 41 905, DE-AS No. 21 15 979, DE-AS No. 25 32 503). All known light collecting arrangements have the characteristic that the angle of the incident radiation must be influenced so that the radiation initially entering within the limiting angle of the arrangement is propagated outside of this limiting angle. For light conducting rods this limiting angle is the limiting angle for total reflection.

It is known, in connection with known light conducting rod arrangements, to roughen the light entry side surface in the manner of frosted glass (German Auslegeschrift DE-AS No. 21 15 979) in order to deflect light which impinges on the side surface of the rod substantially normally to the rod axis at angles of total reflection into the interior of the rod. In addition, one has already arranged light scattering material on the side surface of the light conducting rod diametrically opposite to the light inlet in order to deflect the incident light out of the direction of incidence (Austrian patent specification AT-PS 206 663). It is a disadvantage of these two known light conducting rod arrangements that a large fraction of the incident light is not deflected into angular ranges of total reflection and is thus lost for measurement purposes.

For this reason one has already provided a stepped mirror arrangement on the side surface of the light conducting rod diametrically opposite to the light inlet (German patent application DE-AS No. 25 32 603). The individual mirrors of this stepped mirror arrangement are so directed relative to the longitudinal axis of the light conducting rod that all the incident light is deflected at angles of total reflection into the interior of the light conducting rod. These light conducting rods are also not completely satisfactory because the relatively coarse mirror raster gives rise to a disturbing modulation when a scanning light beam periodically scans along the longitudinal axis of the light conducting rod. As a result of secondary beams these light conducting rods have a restricted efficiency which falls off strongly for light beams which deviate increasingly from the direction of normal incidence.

The light collecting surface of all known light collecting arrangements consists, in general, of one or more photoelectric converters which provide an electrical signal corresponding to the amount of incident light. It is thus important, in all light collecting arrangements, to ensure that as much as possible of the light incident at one or another point along their lengths reaches the light collecting surface. Furthermore, it is important that light incident at the same angles at different points of the elongate optical light deflecting device should produce an electrical signal of the same strength at the photoelectric converter.

Such light collecting arrangements are in general arranged parallel to a material web which is scanned periodically with a light bead by means of a laser beam. The light reflected from the material web, or passing through the material web is then picked up by the light collecting arrangement and deflected to the photoelectric converter. The electrical output signal of the photoelectric converter is evaluated in order to recognize faults in the material web.

The principal object underlying the invention is thus to provide, for a light collecting arrangement of the initially named kind, an elongate optical light deflecting device which does not have the disadvantages of the known devices and which deflects light which is incident at different positions and at the same angles, with high efficiency (i.e. with only low light losses), onto the light collecting surface. Furthermore incident light beams which lie within the desired angular range should all be deflected in the same manner irrespective of their precise angle or the point at which they fall on the light deflecting device so that a uniform electrical output signal is achieved. When using the light collecting arrangement with a material web which is periodically scanned by a scanning light bead the electrical output signal of the photoelectric converter should not show any notable modulation.

In order to satisfy this object the invention proposes that the light deflecting device should take the form of a diffraction grating. The diffraction grating should, in particular, be constructed as a hologram, and preferably a volume hologram, of such a thickness, that all the light beams incident within the predetermined angular range are transmitted and subjected to deflection whereas light beams which lie outside this angular range are not. It is of particular advantage for the hologram to be a phase hologram.

In principle the diffraction grating can be a periodic two-dimensional or three-dimensional grating.

As a hologram can be readily manufactured with sinusoidally changing transmission or reflection characteristics, or refractive index, it is possible for light beams which are incident on the light deflecting device at a specified angle to be deflected at a specified angle of emergence onto the light collecting surface. For this purpose the hologram is produced by superimposing a reference wave and an object wave in a photosensitive material. The direction of the reference wave corresponds to that of the incident light in the light collecting arrangement of the invention. In this manner the light emerges from the hologram in the same direction as the object wave enters the light sensitive material when producing the hologram. So long as the intensity is selected when illuminating the hologram in such a way that the limits of the range of linearity of the photographic material are not exceeded the recorded interference patterns are strictly sinusoidal and no higher diffraction orders arise. If the hologram is thick relative to the wavelength one of the two symmetrical first diffraction orders will also be suppressed so that the hologram only generates one output wave.

The thickness of the hologram is an important factor in providing a practical embodiment of a light collecting arrangement in accordance with the invention. For thin phase holograms efficiencies from 33% to over 50% can be achieved with a thickness of a few wavelengths. For a thick hologram, in which the thickness is a multiple of the wavelength, efficiencies up to almost 100% can be achieved. Because of the necessity of observing the Bragg condition thick holograms however only pass light beams which enter the hologram in a narrow angular range about the angle of the reference wave. This angular range becomes larger as the hologram becomes thinner. One can thus specify the angle cut-off sharpness of the diffraction grating from the outset by an appropriate thickness of the hologram. For such cases, in which a low angular cut-off sharpness is desired, one can achieve high efficiencies even for a thin hologram by a pronounced modulation of the material. A suitable material for this purpose is, for example, dichromatic gelatine with which efficiencies of almost 90° can be achieved even for a thickness of only 5 $\mu$m.

For the purposes of the invention the ideal thickness of the hologram occurs when the angular range in the plane of incidence which is to be detected by the light collecting arrangement is transmitted but not however light beams the angles of which lie beyond this angular range. The light collecting arrangement of the invention can thus be used as a selective angular range filter in as much as it transmits one specific angular range but not however another. This advantageous characteristic of the diffraction grating of the invention can be used for the recognition of faults.

The invention can be used with advantage with light collecting arrangements in which the angular range is orientated in the same manner to the longitudinal direction at all points along the light deflecting device. This case arises, by way of example, for fault detecting devices for material webs in which the material web is scanned by a sharply defined light beam which is displayed parallel to itself. In this case light leaves all the fault-free points of the material web within the predetermined angular range and can then be deflected in uniform manner to a photoelectric converter by the light collecting arrangement of the invention by using a diffraction grating which has the same grating constant over its whole length. It is naturally important for all embodiments that the frequency of the light detected by the light collecting arrangement of the invention is matched to the grating constant of the diffraction grating.

A particular advantage of the light collecting arrangement of the invention resides in the fact that it can also be used with advantage when the orientation of the angular range relative to the longitudinal direction differs at at least some points along the light deflecting device. In this case the grating constant of the diffraction grating namely only needs to change in the longitudinal direction in such a way that the deflected beams have substantially the same direction despite the changing orientation of the angular range at all points along the longitudinal direction. In situations in which, even for a fault free web, the angular range of the light leaving the material web is different at some positions than at others it is possible to deflect the light beams reflected from the web (or passing through the web) somewhat differently by changing the grating constant in this region so that all normally (regularly) incident light beams extend at the same angles to the longitudinal axis of the light deflecting device.

This embodiment is particularly suitable for use with light collecting arrangements in which it is desired to deflect light coming from a material web which is scanned by a scanning beam moving in a sector-like fashion. In this case the grating constant continuously increases or decreases, in accordance with the invention, in dependence on the angle of incidence on the web in order to achieve a substantially constant direction of all the deflected beams. Thus, in accordance with the invention, the expensive concave mirror, which is normally necessary to produce a scanning light beam which is displaced parallel to itself, can be omitted in the simplest possible manner, without deleteriously affecting the quality of the fault recognition because the different angles of impingement of the sector-like sharply defined light beam on the surface of the web can be readily taken into account by varying the grating constant.

The invention can also be advantageously combined with a preferably round light conducting rod extending parallel to the light deflecting device and in optical contact therewith. In this application the angle of deflection of all light beams within the predetermined angle range is sufficiently large, in accordance with the invention, that the light beams extend at angles of total reflection to the wall of the light conducting rod. It is thus possible, when the grating lines change sinusoidally and the thickness of the diffraction grating is ideally matched to the angular range which is to be detected, to achieve a high efficiency with regard to the light which enters into angles of total reflection.

The diffraction grating can be arranged both on the light inlet side surface and on the side surface diametrically opposite to the light inlet. In the latter case the diffraction grating is constructed as a reflection grating.

In a completely new arrangement the diffraction grating is however embedded in the light conducting rod along the axis thereof with the width of the embedded diffraction grating being preferably only equal to a fraction of the diameter of the light conducting rod.

It is advantageous, in particular with the last named embodiment for the light which is incident in the middle of the predetermined angular range to be deflected by an angle of approximately 90° into the light conducting rod. In these embodiments the small losses which still occur on total reflection can be avoided almost completely. As the light which is reflected or transmitted from a scanned material web is not only scattered in the plane of incidence, but instead within a solid angle, it is in any event expedient if the divergent light beams, which are located in known manner in planes at right angles to the rod axis, are concentrated onto the diffraction grating by a cylindrical lens arranged parallel to the light conducting rod, and if necessary, by the round light conducting rod itself.

The invention is also basically suitable for detecting continuous lines of light on material webs.

The invention will now be described by way of example in the following with reference to the drawings which show.

Figure 1:
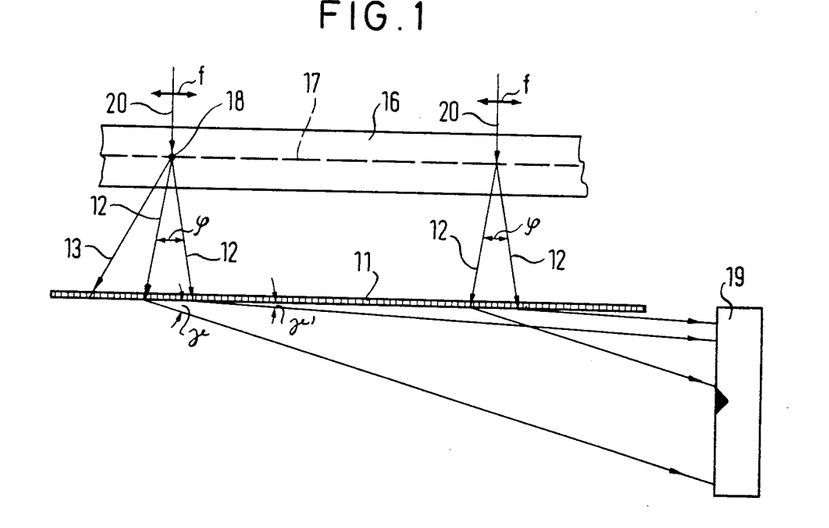
FIG. 1 a schematic side view of a first embodiment of a light collecting arrangement in accordance with the invention and without a light conducting rod, it being assumed that a scanning light beam which is displaced parallel to itself is used to generate a scanning light bead on a material web, FIG. 2 a view analogous to that of FIG. 1 in which however a scanning beam is used which is pivoted to and fro within a sector, FIG. 3 a view analogous to that of FIG. 1 showing a light collecting arrangement in accordance with the invention operating with a light conducting rod, FIG. 4 a view similar to that of FIG. 3 showing a somewhat different construction of the diffraction grating, FIG. 5 a schematic cross-section of the subject of FIG. 4, FIG. 6 a view analogous to that of FIG. 3 of a further embodiment with a diffraction grating arranged at the light inlet side, FIG. 7 a schematic cross-section of the subject of FIG. 6, FIG. 8 a view analogous to FIG. 3 with the diffraction grating being arranged at the side surface of the light conducting rod diametrically opposite to the light inlet, FIG. 9 a schematic cross-section of the subject of FIG. 8, FIG. 10 a view corresponding to that of FIG. 6 in which a scanning beam is used which executes a sector-like movement, and FIG. 11 a schematic illustration of the manufacturing process for producing a diffraction grating in accordance with the invention.

As seen in FIG. 1 a sharply defined laser beam 20 of predetermined frequency moves to and fro in the direction of the double arrow f and scans a material web 16 transversely to its longitudinal direction along a scanning line 17. At each successive moment a sharp light bead 18 is thus generated on the surface of the material web 16 at a different point on the scanning line 17. The light is reflected from the surface of the material web 16, in particular at the angle of reflection, in the form of reflected beams 12, 13. It is however equally possible to allow the light to pass in a straight line through a transparent material web. The scanning beam 20 can be generated, by way of example, in the manner described in German laying open print DE-OS No. 24 33 682.

As a result of the individual characteristics of the material web 16 the reflected or transmitted light will be scattered within an angular range $\phi$ in the plane of reflection or transmission.

As shown in FIG. 1 a diffraction grating 11 is arranged parallel to the scanning line 17 and the diffraction characteristics of this diffraction grating are chosen so that, for a predetermined frequency of the light, the light beams 12 impinging within the angular range $\phi$ are subjected to a sharp deflection at angles $\gamma$ to $\gamma'$. A photosensitive converter 19 which forms the light gathering surface is placed in the path of all these deflected light beams and thus receives all the light which is incident within the predetermined angular range $\phi$ at different points along the length of the diffraction grating 11 and indeed independently of the point at which the light impinges on the diffraction grating 11. By way of example two different positions of the scanning beam 20 which is displaced parallel to itself are reproduced in FIG. 1. The smallest surface area for the converter is achieved for a mean angle $\gamma = 0$.

Figure 2:
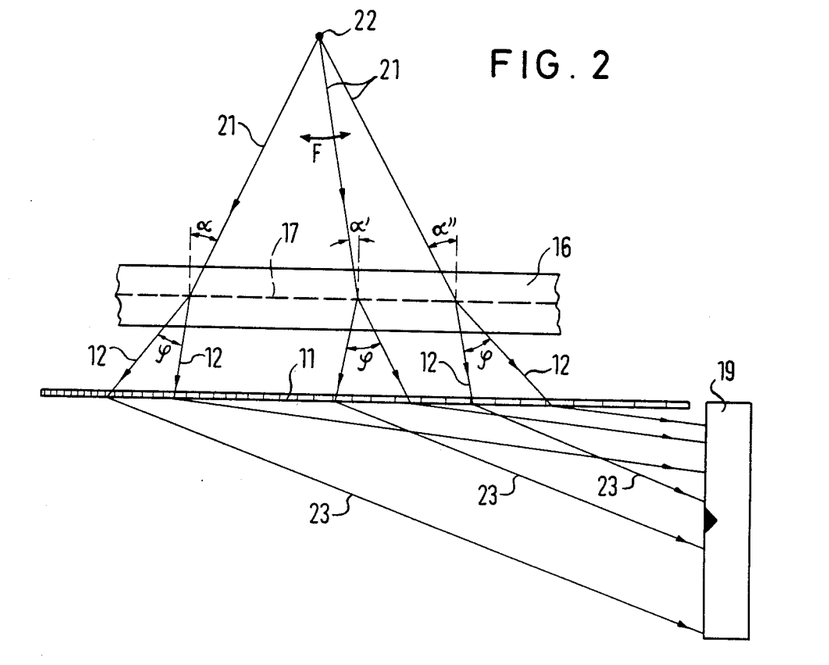

FIG. 2 illustrates, in schematic form, a scanning light beam 21 which starting from a point 22 executes a sector-like scanning movement in the direction of the double arrow F. By way of example an oscillating mirror which is illuminated by a laser beam from a fixed light source can be arranged at the point 22. As a result of this arrangement the scanning light beam 21 falls on the scanning line 17 of the material web at different angles $\alpha$, $\alpha'$ or $\alpha''$ depending on the angular position of the scanning light beam. Accordingly, the angular ranges $\phi$ for the light scattered from the material web are arranged at different angles to the diffraction grating 11. In order to compensate for this, the diffraction grating 11 has a grating constant which reduces in the direction from left to right in FIG. 2 as is schematically illustrated in a simple manner by the increasing spacing of the grating lines from left to right. Accordingly, the light beams which fall on the diffraction grating 11 further to the left are more strongly deflected than the light beams which fall on the diffraction grating 11 at the centre or further to the right.

The emergent light beams 23, which respectively correspond to the same incident light beams, emerge at the same angles from the diffraction grating 11 as a result of suitable variation of the grating constant and fall on the photoelectric converter 19 in the same manner as for the embodiment of FIG. 1. The continuous change in the angular position of the scanning light beam 21 can thus be compensated for in the simplest of manners.

Figure 11:
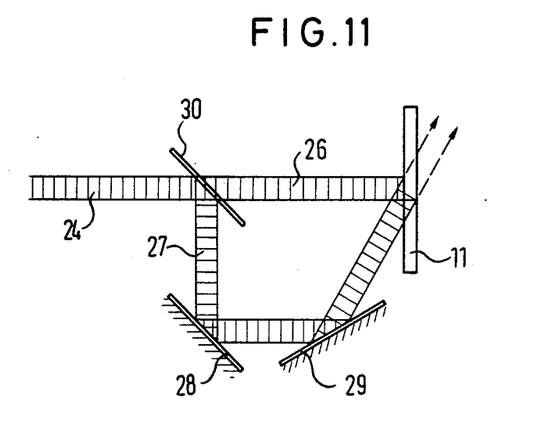

The production of a diffraction grating suitable for the purposes of the invention is illustrated schematically in FIG. 11. A coherent plane wave of predetermined frequency, which can for example be formed by a widened laser beam, falls on a partially transmitting mirror 25 and is split by this mirror into a reference wave 26 and an object wave 27. The object wave is caused to intersect with the reference wave 26 by repeated reflection at plane mirrors 28, 29 in the manner which can be seen from FIG. 11. A photosensitive material 11 is placed at the point of intersection and the interference pattern caused by the intersection of the waves 26, 27 is latently recorded in the photosensitive material. After developing, a diffraction grating in the form of a volume hologram is present. On illuminating this hologram with a light beam corresponding to the reference wave 26 the object wave is reproduced in the manner illustrated in broken lines in FIG. 11. It is thus possible to realize practically any desired angle of deflection by suitable manufacture of the hologram so that, in accordance with the invention, one is able to use relatively small area photoelectric converters 19 in particular when the angular range $\phi$ which is to be deflected is relatively narrow.

The angular range $\phi$ transmitted by the hologram 11 depends on the thickness of the hologram. The thicker the hologram is the greater the angular selectivity. The hologram 11 is ideally constructed when only the predetermined angular range $\phi$, together with the marginal rays 12, is transmitted but not a beam 13 (FIGS. 1 and 2) which is incident at a larger angle.

A relatively thick phase hologram is above all advantageous because its efficiency is relatively high. The transmitted angular range $\phi$ is, however, then relatively restricted.

Figure 3:
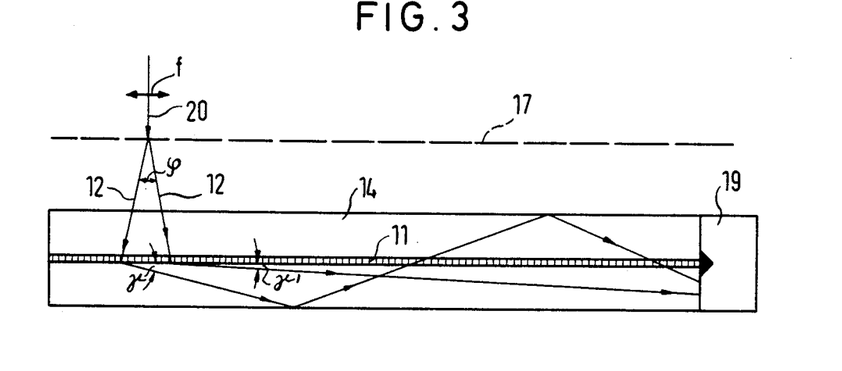

In order to be able to use a photoelectric converter 19 which is not too large in area, even with relatively large angular ranges $\phi$, the diffraction grating of the invention is embedded as shown in FIG. 3 in a light conducting rod 14 of round cross-section. The extreme deflection angles $\gamma$, $\gamma'$ are so selected that the light of all the incident light beams 12 enter into the light conducting rod 14 at angles of total reflection. Substantially all this light therefore reaches the photoelectric converter which is optically coupled to the end of the light conducting rod. A photoelectric converter 19 can also be arranged at the oppositely disposed end face. A mirror surface can, however, also be present at this point.

Figure 4:
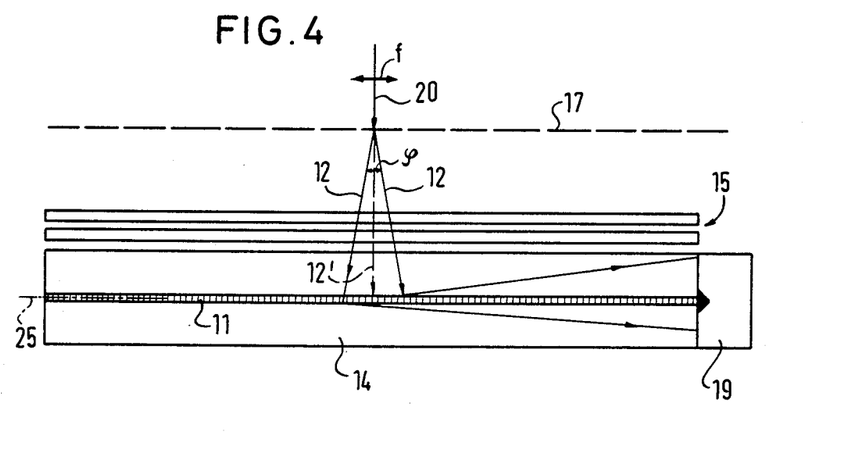

FIG. 4 shows how the grating constant of the diffraction grating 11 can be optimized by arranging the diffraction grating in a light conducting rod 14. The grating constant is namely selected in this instance such that the central incident light beam 12', which is incident at right angles to the rod axis 25, is deflected exactly in the direction of the rod axis 25, i.e. through a right angle. The marginal beams 12 of the angular range $\phi$ thus extend only at relatively small angles to the axis 25 so that they reach the photoelectric converter 19 substantially without undergoing a single total reflection. If a single total reflection occurs then it takes place at such a small angle that practically no losses occur.

Figure 5:
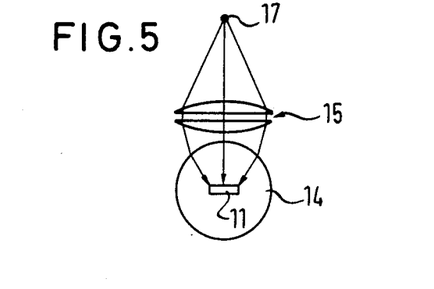

As seen in FIGS. 4 and 5 a cylindrical lens 15 is arranged in front of and parallel to the light conducting rod. The purpose of the cylindrical lens 15 is to concentrate, together with the refractive effect of the round light conducting rod 14, the light which is also scattered from the web in the plane at right angles to the rod axis 25 onto the surface of the diffraction grating 11 in the manner shown in FIG. 5 and thus to fully utilize this light for the measurement. It can also be seen from FIG. 5 that the diffraction grating 11 which is embedded in the light conducting rod 14 is relatively narrow when compared with the diameter of the light conducting rod 14.

Figure 6:
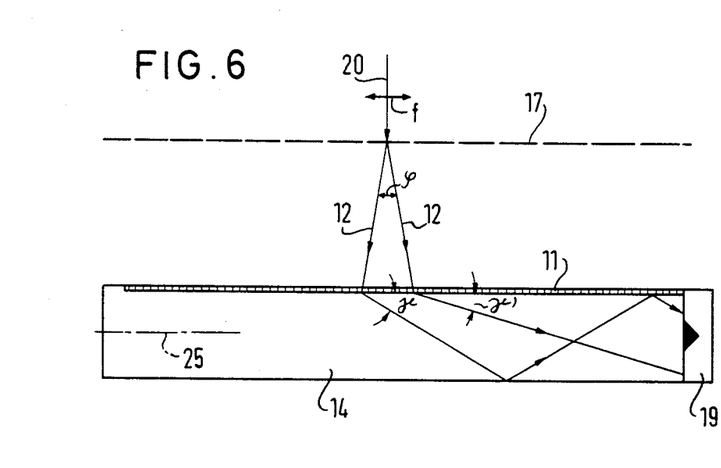
Figure 7:
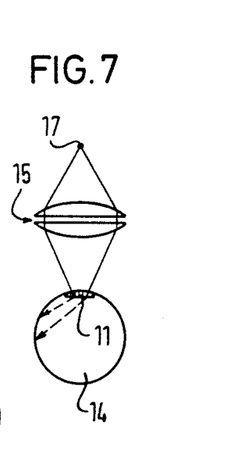

As seen in FIGS. 6 and 7 the diffraction grating 11 is arranged in a narrow zone of the light inlet side surface of the light conducting rod 14. In this case it is expedient for the angle of deflection $\gamma'$ to tend to zero in order to avoid total reflections and, where they occur, to achieve as shallow an angle of light incidence as possible.

As seen in FIG. 7 the refractive power of the cylindrical lens 15 must be somewhat greater than for the embodiment of FIGS. 4 and 5 because the refractive power of the round light conducting rod 14 does not in this instance assist in concentrating the light beams emerging from the scanning line 17 in planes at right angles to the rod axis 25.

Figure 8:
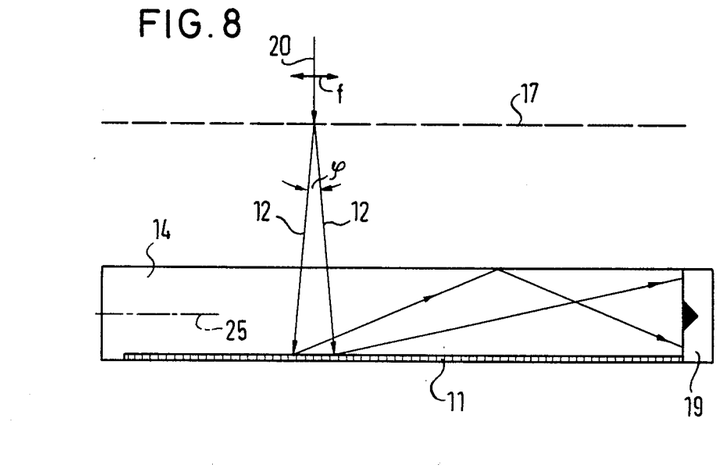
Figure 9:
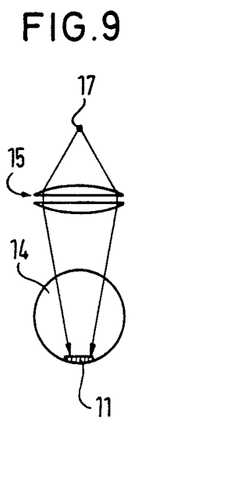

FIGS. 8 and 9 show that the diffraction grating of the invention can also be arranged at the side surface of the light conducting rod in optical contact with the light conducting rod and diametrically opposite to the light inlet. The diffraction grating 11 is in this case constructed as a reflection grating which can also be manufactured in accordance with a method analogous to that of FIG. 11.

As seen in FIG. 9 the refractive power of the light conducting rod 14 can once again be jointly used to concentrate the convergent light in planes at right angles to the rod axis 25 so that, in this embodiment, similar conditions prevail as for the embodiment of FIGS. 4 and 5. For the embodiment of FIGS. 8 and 9 the refractive power of the cylindrical lens 15 does not however need to be quite as large as for the embodiment of FIGS. 4 and 5 because the diffraction grating 11 is spaced further from the light inlet side.

Figure 10:
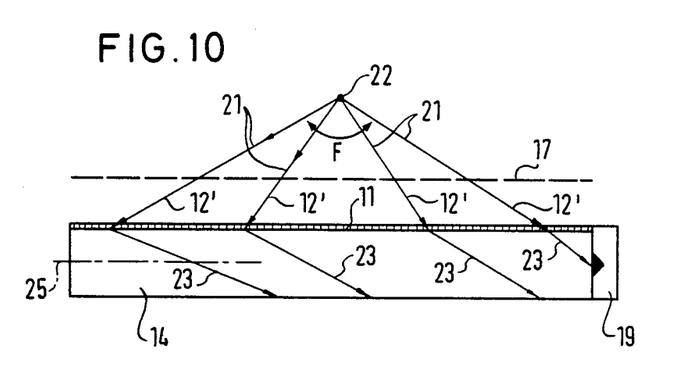

FIG. 10 shows that a scanning beam 21 which executes a sector-like scanning movement in accordance with FIG. 2 can also be used with a light collecting arrangement in accordance with the invention and incorporating a light conducting rod. A light conducting rod analogous to the embodiment of FIGS. 6 and 7 is shown in FIG. 10 with a diffraction grating 11 analogous to that of FIG. 2 arranged at the light inlet side of the light conducting rod so that light beams falling at different angles on the diffraction grating 11 also enter the light conducting rod 14 as emergent beams 23 at a constant angle to the rod axis. The total reflection conditions are thus the same for all the deflected beams 23 so that, if the inlet light beams are of the same intensity, a corresponding electrical signal is also achieved at the output of the photoelectric converter 19. For the sake of simplicity only the central reflected beams 12' from the scanning line 17 are shown in FIG. 10 whereas the actual prevailing angular range $\phi$ of the preceding embodiments has been omitted to make the drawing less complicated.

The diffraction grating of the invention can also be manufactured by photographic or mechanical means. It is also possible to copy an already existing grating photochemically or thermoplastically or holographically.

When the grating is "geblazt", i.e. when the grating has preferred directions of reflection, as a result of its mechanical construction, deflection efficiencies over 50% can be achieved for a surface phase grating.

It should also be remarked, in connection with the embodiment of FIG. 4 in which the deflected light beams extend substantially parallel to the rod axis 25, that it is ensured, in the case of a thick diffraction grating 11, as a result of the Bragg condition, that light reflected at the rod no longer changes its direction in a disadvantageous manner on renewed passage through the grating 11 because of the specular angle of reflection that arises.

Efficiencies up to nearly 100% can be achieved as a result of the construction in accordance with the invention. As a result of the short periodic length of the grating of ca. one half a wavelength of the light that is used, no modulation of the deflected light occurs. Approximately the same precision of measurement can be achieved with a scanning light beam effecting a sector-like scanning movement as for a scanning light beam which is displaced parallel to itself. A filter effect with respect to the transmitted angular ranges can be achieved by appropriate choice of the thickness of the diffraction grating.

The light collecting arrangement of the invention enables in particular a cost saving with regard to the light conducting rod and the whole system. The reliability of fault recognition is significantly increased.

The deflection of the central beam of an angular range in a direction parallel to the diffraction grating has the advantage, both in the embodiment with and also the embodiment without a light conducting rod, that the light of the central beam does not propagate to the end of the diffraction grating but is instead successively scattered sideways. This light therefore does not reach the photoelectric converter provided in the region at the end of the diffraction grating. This is of great advantage for fault recognition when the central beam corresponds to the normal, undistorted reflection, or the normal, undistorted passage of the light through the material web, and faults make themselves noticible by greater or lesser deflection of the light. In other words the invention makes a kind of dark field illumination possible by eliminating the very intensive central light beam. In addition comes the advantage that the photoelectric receiver can have the minimum possible surface when the central beam is deflected in the said manner in a direction parallel to the diffraction grating.

A particular advantage of using holograms as diffraction gratings resides in the fact that one is free with regard to the selection of the direction of the reconstructed wave. FIG. 7 shows for example how, in the plane extending at right angles to the longitudinal direction, the angle of deflection of the incident light can be so selected that the deflected beam falls at a large angle on the side surface of the round light conducting rod and the fraction which falls back on the hologram after multiple reflection is small. The deflected light is illustrated in broken lines in FIG. 7. Any other desired form of deflection can also be realized in this plane.

We claim:

1. A light collecting arrangement in combination with a light scanning arrangement for inspecting a web of material using a laser light beam of predetermined frequency, wherein the light collecting arrangement comprises: a light collecting surface and an elongate optical light deflecting device, said device having first and second spaced apart ends and an elongate light entry side surface extending between said first and second spaced apart ends in a longitudinal direction substantially at right angles to said light collecting surface; wherein said light collecting surface is arranged at one of said first and second ends; wherein said light entry side surface lies in a plane of incidence; wherein said device comprises an elongate hologram extending in said longitudinal direction parallel to said elongate light entry side surface within said plane of incidence; and wherein said hologram is constructed by interference in a photosensitive material of a reference wave and an object wave of the same frequency as said predetermined frequency of said laser beam, with said object wave extending relative to said photosensitive material at an angle corresponding to the desired direction of light deflected by said hologram to said light collecting surface and with said reference wave extending relative to said photosensitive material at an angle corresponding to the desired direction of light which is to be deflected by said hologram towards said light deflecting surface; whereby light beams which leave said material web, which lie within a predetermined range of angles in said plane of incidence and which are incident at any point along said light entry side surface with a significant component normal to said longitudinal direction are deflected substantially exclusively at angles at which they reach said light collecting surface; whereas light beams lying outside of said predetermined range of angles are deflected at angles at which they do not reach the light collecting surface.

2. The combination in accordance with claim 1 wherein the hologram is a phase hologram of such a thickness that all the light beams incident within the predetermined angular range are transmitted and subjected to deflection toward the light collecting surface, whereas light beams which lie outside this angular range are not deflected toward the light collecting surface.

3. The combination in accordance with claim 1 wherein the angle of deflection is constant at all points along the light deflecting device and wherein the hologram has the same deflection characteristics over its whole length.

4. The combination in accordance with claim 1 wherein there is further provided a round light conducting rod extending parallel to said elongate optical light deflecting device and in optical contact therewith, and wherein the deflection angles of all the light beams within the predetermined angular range are so large that these light beams extend at angles of total reflection to the wall of the light conducting rod.

5. The combination in accordance with claim 4 and wherein the hologram is arranged on the light entry side surface of the light conducting rod.

6. The combination in accordance with claim 4 and wherein the hologram is arranged on the side surface of the light conducting rod opposite to the light entry surface and is constructed as a reflective hologram.

7. The combination in accordance with claim 4 and wherein the hologram is embedded in said light conducting rod along the axis thereof.

8. The combination in accordance with claim 7 and wherein the width of the embedded hologram amounts only to a fraction of the diameter of the light conducting rod.

9. The combination with claim 4 and wherein light incident at an angle in the middle of said predetermined angular range is deflected through an angle of approximately 90°.

10. The combination in accordance with claim 4 and wherein the divergent light beams which are located in planes at right angles to the rod axis are concentrated onto the hologram by a cylindrical lens arranged parallel to said light conducting rod.

11. The combination in accordance with claim 1 and wherein the light beams at the mid-point of the angular range are deflected to said light collecting surface directly.

12. A light collecting arrangement in combination with a light scanning arrangement for inspecting a web of material using a laser light beam of predetermined frequency, wherein the light collecting arrangement comprises: a light collecting surface and an elongate optical light deflecting device, said device having first and second spaced apart ends and an elongate light entry side surface extending between said first and second spaced apart ends in a longitudinal direction substantially at right angles to said light collecting surface; wherein said light collecting surface is arranged at one of said first and second ends; wherein said light entry side surface lies in a plane of incidence; wherein said device comprises an elongate hologram extending in said longitudinal direction parallel to said elongate light entry side surface within said plane of incidence; and wherein said hologram is constructed by interference in a photosensitive material of a reference wave and an object wave of the same frequency as said predetermined frequency of said laser beam, with said object wave extending relative to said photosensitive material at an angle corresponding to the desired direction of light deflected by said hologram to said light collecting surface, said desired direction varying at at least some points along the light deflecting device, and with said reference wave extending relative to said photosensitive material at an angle corresponding to the desired direction of light which is to be deflected by said hologram towards said light deflecting surface; wherein the deflection characteristics of the hologram vary in the longitudinal direction in such a way that the deflected beams have substantially the same direction despite having different incidence angles at various points along the longitudinal direction; and wherein light beams which leave said material web, which lie within a predetermined range of angles in said plane of incidence and which are incident at any point along said light entry side surface with a significant component normal to said longitudinal direction, are deflected substantially exclusively at angles at which they reach said light collecting surface whereas light beams lying outside of said predetermined range of angles are deflected at angles at which they do not reach the light collecting surface.

13. The combination in accordance with claim 12 wherein said light scanning arrangement comprises means for generating from said laser beam a scanning beam which scans said material web in sector-like fashion, and wherein the deflection characteristics of the hologram continuously change in accordance with the angle of incidence ($\alpha$, $\alpha'$, $\alpha''$) on the web in order to achieve a substantially common direction for all the deflected beams.

* * * * *